United States Patent
Huang

[19]

[11] Patent Number: 6,093,171
[45] Date of Patent: Jul. 25, 2000

[54] SAFETY SYRINGE

[76] Inventor: Wu-Shun Huang, 7F, 295, Sec. 2, Ho-Ping E. Rd., Taipei, Taiwan

[21] Appl. No.: 09/475,955

[22] Filed: Dec. 30, 1999

[51] Int. Cl.⁷ ...................................................... A61M 5/00
[52] U.S. Cl. ........................................... 604/110; 604/195
[58] Field of Search ................................... 604/110, 187, 604/192, 198, 195, 263, 218

[56] References Cited

U.S. PATENT DOCUMENTS

| | | | |
|---|---|---|---|
| 5,047,016 | 9/1991 | Dolgin et al. | 604/195 |
| 5,215,533 | 6/1993 | Robb | 604/195 |
| 5,395,346 | 3/1995 | Maggioni | 604/195 |
| 5,405,327 | 4/1995 | Chen | 604/110 |
| 5,634,903 | 6/1997 | Kurose et al. | 604/110 |
| 5,693,023 | 12/1997 | Adams | 604/195 |
| 5,785,687 | 7/1998 | Saito | 604/110 |

Primary Examiner—John D. Yasko
Attorney, Agent, or Firm—Rosenberg, Klein & Lee

[57] ABSTRACT

A safety syringe that is characterized by that a plunger thereof has an elastic stopper fitted around a neck portion of the plunger near a front end thereof. When the plunger is fully pushed forward in a barrel of the syringe, the stopper slightly deforms to allow the plunger to move forward a little further, so that all medical liquid in the barrel is injected into a patient's body. The safety syringe is also characterized by that an elastic catch hook is provided at the front end of the plunger and a catch rib is provided around a rear inner end of a locking tip that is fitted to a front end of the barrel for a needle to connect thereto. When the plunger is further pushed forward in the barrel, the catch hook is moved beyond the catch rib and retained in the locking tip by the catch rib. Whereby, simply pulling the plunger backward could directly pull the locking tip and a used needle backward into the barrel to avoid injuring others. And, no medical liquid or sucked blood would remain in the used needle to cause a second time contamination.

3 Claims, 6 Drawing Sheets

SAFETY SYRINGE

BACKGROUND OF THE INVENTION

In the medical practices of early days, a used syringe would be thoroughly sterilized for repeated use later. Any incomplete sterilization would dangerously cause a second time infection of a patient and/or any other people. To avoid such second time infection, disposable syringes are largely produced. However, large amount of discarded disposable syringes also bring us new problems of environmental pollution and safety in use. This is because no specific measures have been taken in disposing needles of the discarded syringes and exposed needles tend to easily stab nursing or cleaning personnel and result in even more infected people. To prevent discarded syringes and/or needles from injuring and infecting other people, various kinds of syringes with means for destroying used needles are developed. A typical syringe with such needle destroying means usually includes a plunger having a projected retaining hook to engage with a rear end of a needle holder, so that the needle holder and the used needle could be pulled into a barrel of the syringe. The needle being pulled into the barrel is bent and thereby destroyed. A problem with such syringe is, when the retaining hook on the plunger is about to engage with the rear end of the needle holder, there is still some medical liquid remained between the plunger and the barrel, and when the retaining hook gets in contact with the rear end of the needle holder, an air-tight space is formed in the barrel that prevents the retaining hook on the plunger from successfully engaging with the rear end of the needle holder. Clinically, a nursing personnel must first pull the needle out of the patient's body and then pushes the plunger further to engage the retaining hook with the rear end of the needle holder. At this point, medical liquid and/or patient's blood that presents in the barrel and/or the needle would jet out from the needle when the plunger is pushed forward. And, the jetted blood forms another form of contamination endangering other people.

SUMMARY OF THE INVENTION

It is therefore a primary object of the present invention to provide an improved safety syringe that includes a plunger having an elastic stopper made of soft rubber material fitted around a neck portion of the plunger near a front end thereof, so that when the plunger is fully pushed forward in a barrel of the syringe, the stopper slightly deforms to allow the plunger to move forward a little further, so that all medical liquid in the barrel is injected into a patient's body.

Another object of the present invention is to provide the above improved safety syringe that further includes an elastic catch hook provided at the front end of the plunger and a catch rib provided around a rear inner end of a locking tip (or needle holder) that is fitted to a front end of the barrel for a needle to connect thereto, so that when the plunger is further pushed forward in the barrel, the catch hook is moved beyond the catch rib and retained in the locking tip by the catch rib. Whereby, simply pulling the plunger backward could directly pull a used needle and the locking tip backward into the barrel to avoid injuring a user. And, no medical liquid or blood would present in the used needle to cause a second time contamination or infection.

A further object of the present invention is to provide the above improved safety syringe in which the catch hook on the plunger is designed to possess a certain degree of elasticity and has a conic shape, so that the catch hook could be smoothly moved beyond the catch rib while the plunger moves forward stably. Therefore, when the plunger is pushed forward further to move the catch hook beyond the catch rib, no extra force would be applied on the syringe to cause discomfort to the patient.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
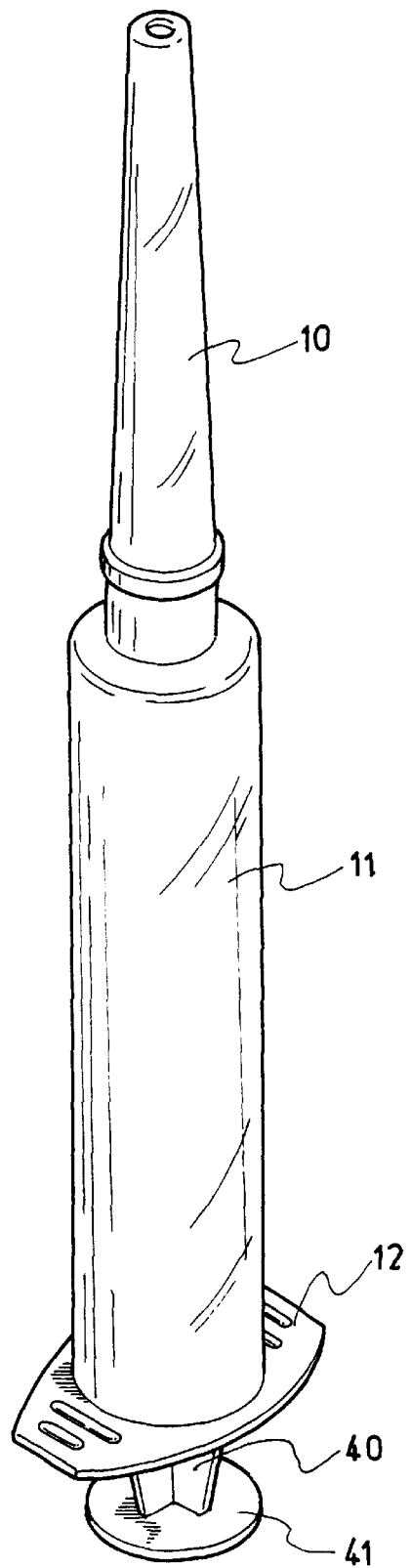
FIG. 1 is a perspective showing the appearance of a safety syringe according to the present invention.
Figure 2:
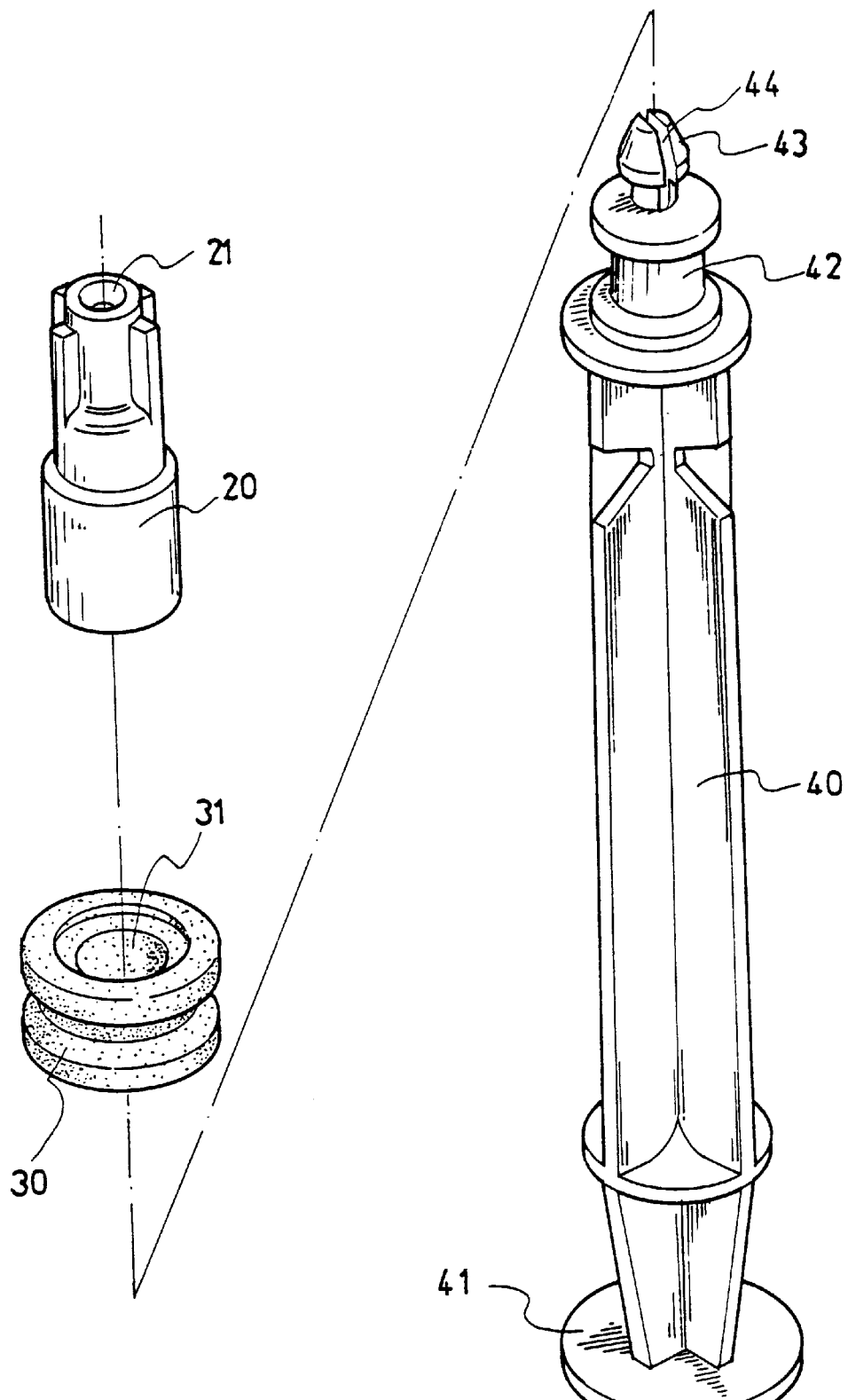
FIG. 2 is an exploded perspective showing disassembled locking tip, stopper and plunger of the syringe of FIG. 1.
Figure 3:
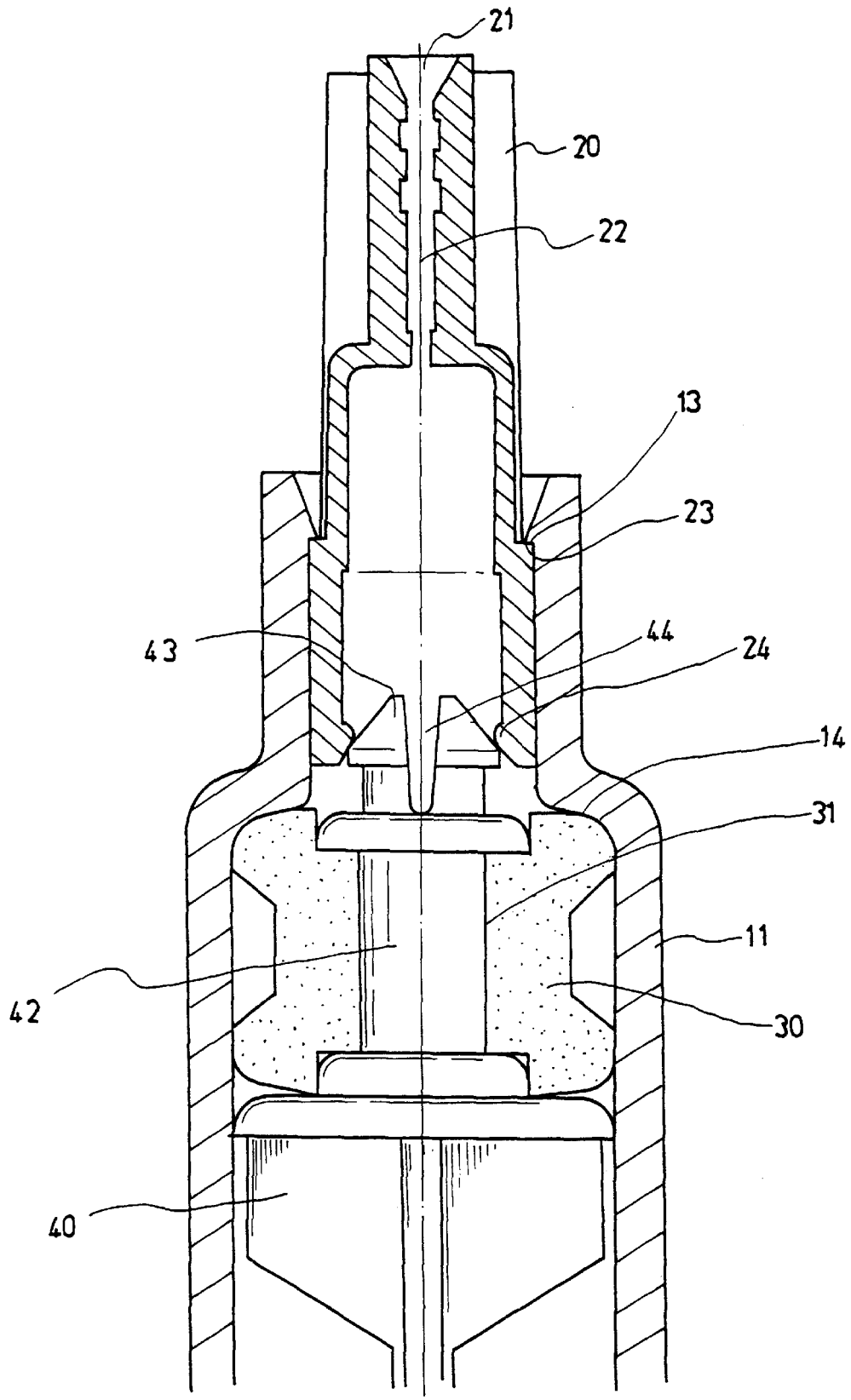
FIG. 3 is a fragmentary and enlarged sectional view of the locking tip, the stopper and the plunger in an assembled state, wherein a catch hook in front of the plunger has not moved beyond a catch rib around a rear inner end of the locking tip.
Figure 4:
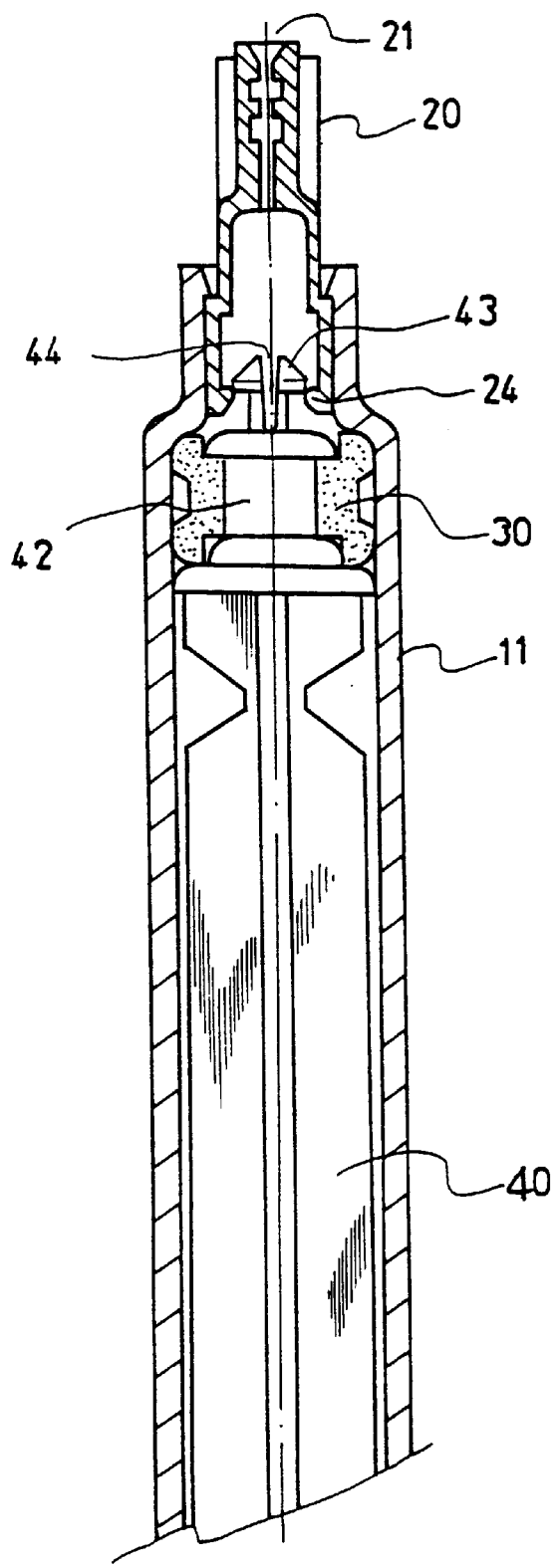
FIG. 4 is a fragmentary sectional view of the safety syringes of the present invention in an assembled state, wherein the catch hook has moved beyond the catch rib and the locking tip is in a normal position for use.

Please refer to FIGS. 1 to 5 in which a safety syringe according to the present invention is shown. The safety syringe mainly includes a barrel 11, a locking tip 20 fitted to a front inner end of the barrel 11 for a needle 50 to connect thereto (see FIG. 5), a needle cap 10 removably covered on the needle 50, a plunger 40 slidably disposed in the barrel 11, and a stopper 30 mounted around a front portion of the plunger 40.

The barrel 11 has a finger flange 12 provided at its rear end and a radially inward projected rib 15 around a rear inner periphery in front of the finger flange 12 (see FIG. 5) for convenient operation of the syringe. The barrel 11 also has a narrowed head portion so that a shoulder portion 14 is formed between the head portion and a rear part of the barrel 11. A front inner end of the head portion has a reduced internal diameter to form an annular stop wall 13 between the front inner end and the rest part of the head portion.

The locking tip 20 has a stepped portion around an outer surface thereof to provide an annular abutting wall 23. A head portion of the locking tip 20 is provided therein with a passage 22 having a front opening 21. The needle 50 is fixed in front of the opening 21. Medical liquid (not shown) in the barrel 11 is supplied to the needle 50 via the passage 22 and the opening 21. The locking tip 20 has a rear inner end around which a radially inward projected catch rib 24 is provided.

The stopper 30 is made of soft rubber material and defines an axially extended through hole 31 therein.

The plunger 40 is provided at a rear end with a thumb rest 41 for easily pushing the plunger 40 forward, and near a front end with a neck portion 42. A generally cone-shaped catch hook 43 is formed in front of the neck portion 42. In an embodiment of the catch hook 43, there is a split 44 provided on the catch hook 43.

The locking tip 20 is fitted in the narrowed head portion of the barrel 11 with the abutting wall 23 abutting against and stopped by the stop wall 13 of the front inner end of the barrel 11 from moving forward any further. The stopper 30 is put around the neck portion 42 so that the latter fitly contacts with an inner wall of the through hole 31 of the stopper 30. By disposing the whole plunger 40 into the barrel 11 via a rear end of the barrel 11 and pushing the plunger 40 forward until a front outer periphery of the stopper 30 is fitly pressed against an inner surface of the barrel at the shoulder portion 14, the syringe of the present invention is ready for use.

When the needle 50 is pierced into a patient's body and a force is applied on the thumb rest 41 to slowly push the plunger 40 forward, medical liquid in the barrel 11 is injected into the patient's body. When the plunger 40 is pushed forward toward the locking tip 20 to press the stopper 30 against the shoulder portion 14 of the barrel 11, the catch hook 43 in front of the stopper 30 is located closely behind the catch rib 24 around the rear inner end of the locking tip 20 and most part of the medical liquid has been injected into the patient's body. Since the stopper 30 is made of soft rubber material and put around the neck portion 42 of the plunger 40, it is possible to push the plunger 40 a little further at this point to inject any remained medical liquid into the patient's body. When the plunger 40 is pushed a little further, the stopper 30 is slightly compressed to allow the catch hook 43 to move beyond the catch rib 24 and engage a rear edge of the cone-shaped head thereof with an inner side of the catch rib 24, so that the catch hook 42 is retained in the locking tip 20 by the catch rib 24 without the risk of moving backward to separate from the locking tip 20. When the catch hook 43 is firmly caught by the catch rib 24, the medical liquid is also completely injected into the body, and there would not have any remained medical liquid and/or blood sucked into the needle 50 to jet from the needle 50 to cause a second time contamination when the needle 50 is pulled out from the patient's body.

The purpose of pushing the plunger 40 forward for a second time is to move the catch hook 43 beyond the catch rib 24. The split 44 on the conic catch hook 43 enables the catch hook 43 to elastically deform and thereby easily pass the catch rib 24 while allow the plunger 40 to move forward in a stable manner without producing a sudden thrust to cause discomfort to the patient. With the engaged catch hook 43 and catch rib 24, a slight backward pulling of the plunger 40 to pull the needle 50 out of the patient's body would not suck blood into the needle 50. The problem of second time contamination caused by remained medical liquid and sucked blood in the needle 50 can therefore be completed eliminated.

What is to be noted is the conic and split catch hook 43 can be smoothly moved beyond the catch rib 24 without effort.

Figure 5:
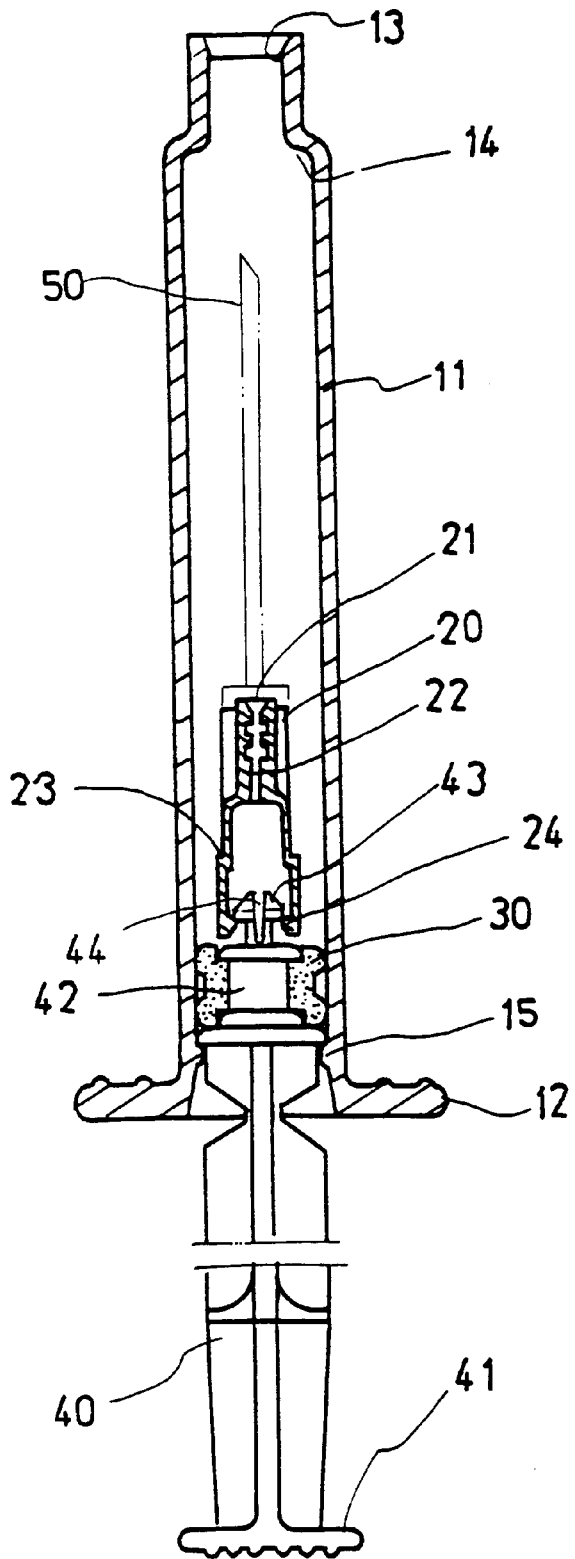
FIG. 5 is a sectional view of the safety syringe of the present invention with the locking pin and a needle connected thereto pulled into the barrel after an injection.

The catch rib 24 is designed to have a curved outer edge and a right-angled inner edge, so that the catch hook 43 can be easily moved beyond the catch rib 24 but can not be easily pulled out from the catch rib 24. With these arrangements, the locking tip 20 may be directly bound to the plunger 40 before the needle 50 is pulled out of the patient's body. Moreover, simply pulling the plunger 40 backward with a minor force could directly pull the whole locking tip 20 and a used needle 50 into the barrel 11 as shown in FIG. 5. The syringe of the present invention is therefore absolutely safe for use.

Figure 6:
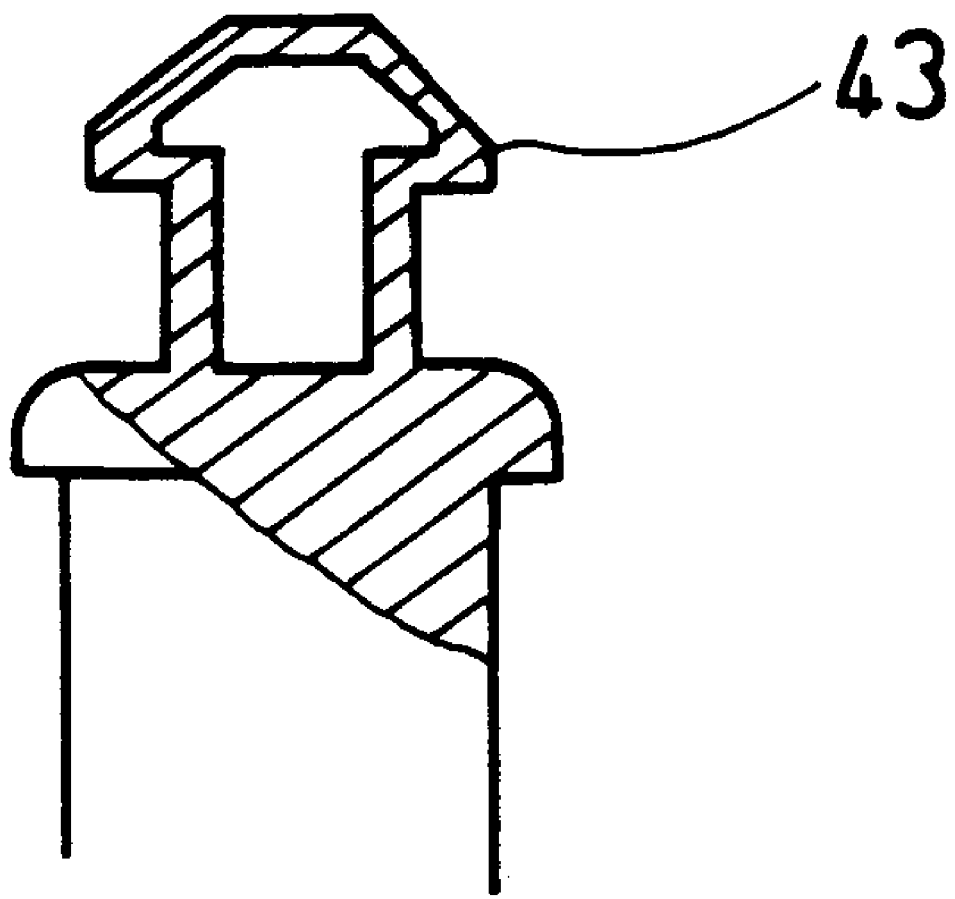
FIG. 6 illustrates a variant of the catch hook used in the present invention.

FIG. 6 illustrates a variant of the catch hook 43. In this variant, the catch hook 43 is a hollow conic body possessing a certain degree of elasticity, so that it can also smoothly move beyond the catch rib 24 and be firmly retained in the locking tip 20 by the catch rib 24. It is understood any other differently shaped catch hooks 43 that provide equivalent effect as that of the above-described catch hooks 43 should be included in the scope of the present invention. And, the present invention may be employed on both a hypodermic syringe and a blood-vessel syringe.

What is claimed is:

1. A safety syringe comprising a barrel, a locking tip fitted in a front inner end of said barrel, a needle connected to a front end of said locking tip, a needle cap removably covered on said needle, a plunger slidably disposed in said barrel, and a stopper fitted around a front portion of said plunger;

said barrel having a narrowed head portion so that a shoulder portion is formed between said head portion and a rear part of said barrel, a front inner end of said head portion having a reduced internal diameter to form an annular stop wall between said front inner end and the rest part of said head portion;

said locking tip having a rear inner end around which a radially inward projected catch rib is formed, said catch rib having a curved outer edge and a right-angled inner edge;

said plunger being provided near a front end with a neck portion, and a generally cone-shaped catch hook being provided in front of said neck portion; and said stopper being made of soft and elastic material and defining an axially extended through hole therein, so that said stopper could by fitted around said neck portion of said plunger.

2. A safety syringe as claimed in claim 1 wherein said cone-shaped catch hook has a split formed on a front end thereof to provide said catch hook with a certain degree of elasticity.

3. A safety syringe as claimed in claim 1, wherein said cone-shaped catch hook is a hollow body to have a certain degree of elasticity.

* * * * *